United States Patent [19]

Seele et al.

[11] Patent Number: 4,963,690
[45] Date of Patent: Oct. 16, 1990

[54] N-AMINOTRIAZOLE DERIVATIVES

[75] Inventors: Rainer Seele, Fussgoenheim; Stefan Karbach, Neustadt-Hambach; Reiner Kober, Fussgoenheim; Matthias Zipplies, Hirschberg; Hubert Sauter, Mannheim, all of Fed. Rep. of Germany; Barbara A. Moore, Pittsboro, N.C.; Dale R. Carlson, Hillsborough, N.C.; Paul S. Zorner, Durham, N.C.; Karl-Otto Westphalen, Speyer; Bruno Wuerzer, Otterstadt, both of Fed. Rep. of Germany

[73] Assignee: BASF Aktiengesellschaft, Ludwigshafen, Fed. Rep. of Germany

[21] Appl. No.: 418,090

[22] Filed: Oct. 6, 1989

[51] Int. Cl.$^5$ ............................................. C07D 249/08
[52] U.S. Cl. .................................. 548/264.8; 546/256; 546/276; 549/426
[58] Field of Search ...................... 548/264.8; 546/276, 546/256

[56] References Cited

U.S. PATENT DOCUMENTS 3,444,162 5/1969 Hyatt ................................. 548/264.8

FOREIGN PATENT DOCUMENTS 283245 9/1988 European Pat. Off. ......... 548/264.8

Primary Examiner—Glennon H. Hollrah
Assistant Examiner—Patricia L. Morris
Attorney, Agent, or Firm—Keil & Weinkauf

[57] ABSTRACT

N-aminotriazole derivatives of the general formulae Ia and Ib

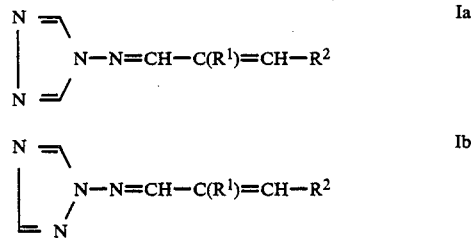

wherein $R^1$ and $R^2$ are each $C_1$–$C_8$-alkyl, $C_3$–$C_8$-cycloalkyl, $C_5$–$C_8$-cycloalkenyl, tetrahydropyranyl or norbornyl, or phenyl, biphenyl, naphthyl or pyridyl, and the aromatic radicals may carry from one to five halogen atoms and/or from one to three of the following groups: hydroxyl, phenoxy, nitro, amino, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, and their salts which are environmentally compatible and tolerated by crops.

3 Claims, No Drawings

N-AMINOTRIAZOLE DERIVATIVES

The present invention relates to N-aminotriazole derivatives of the general formulae Ia and Ib

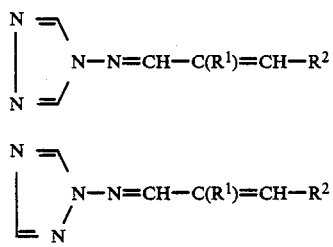

where $R^1$ and $R^2$ are each $C_1$–$C_8$-alkyl, $C_3$–$C_8$-cycloalkyl, $C_5$–$C_8$-cycloalkenyl, tetrahydropyranyl or norbornyl or phenyl, biphenyl, naphthyl or pyridyl, and the aromatic radicals may carry from one to five halogen atoms and/or from one to three of the following groups: hydroxyl, phenoxy, nitro, amino, cyano, $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, and their salts which are environmentally compatible and tolerated by crops.

The present invention furthermore relates to processes for the preparation of compounds Ia and Ib, herbicides which contain N-aminotriazole derivatives as synergistic agents and methods for selectively controlling undesirable plant growth with these herbicides.

The literature discloses that N-aminotriazole derivatives can be used as fungicides (EP-A 283 245).

Herbicidal active ingredients from the group consisting of the benzothiadiazine derivatives of the formula II

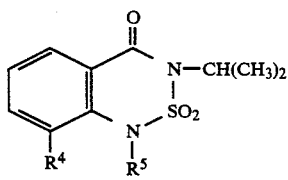

where $R^4$ is hydrogen, halogen, $C_1$–$C_4$-alkyl or $C_1$–$C_4$-alkoxy and $R^5$ is hydrogen or cyano, or their salts which are environmentally compatible and tolerated by crops are used for controlling undesirable plants (DE-A 1 542 836, U.S. Pat. Nos. 158 559, 3 920 441, DE-A 1 918 946, U.S. Pat. Nos. 3 954 437 and 4 464 195).

It is an object of the present invention to provide compounds which increase the action of the above-mentioned herbicides against undesirable plants in a superadditive manner without losing their toleration by crops. Such compounds are referred to in general as synergistic agents.

We have found that this object is achieved by the N-aminotriazole derivatives Ia and Ib defined at the outset.

We have also found methods for controlling undesirable plant growth by using these N-aminotriazoles Ia and/or Ib in conjunction with the herbicides from the group consisting of the benzothiadiazines II, and corresponding agents for controlling undesirable plant growth.

The N-aminotriazoles Ia and Ib contain a trisubstituted double bond. They can accordingly occur in the E and Z configurations.

The novel N-aminotriazole derivatives Ia and Ib are obtainable in various ways.

They are preferably obtained by reacting an N-aminotriazole IIIa or IIIb with a corresponding acrolein derivative IV in a conventional manner in an inert organic solvent in accordance with the following scheme.

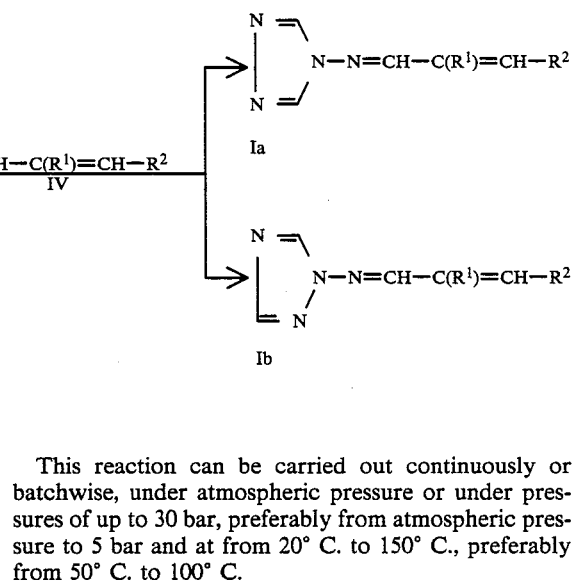

This reaction can be carried out continuously or batchwise, under atmospheric pressure or under pressures of up to 30 bar, preferably from atmospheric pressure to 5 bar and at from 20° C. to 150° C., preferably from 50° C. to 100° C.

Examples of suitable solvents are nitriles, such as acetonitrile and propionitrile, alcohols, such as methanol, ethanol, isopropanol, n-butanol and isobutanol, ethers, such as diethyl ether, diisopropyl ether, tertbutyl methyl ether, dimethoxyethane, dioxane and tetrahydrofuran, and preferably hydrocarbons and halohydrocarbons, such as pentane, hexane, cyclohexane, toluene, methylene chloride, chloroform, carbon tetrachloride, dichloroethane and chlorobenzene.

The acrolein derivatives of the formula III which are required for the reaction are known or can be prepared by the conventional methods of aldehyde synthesis (Houben-Weyl, Vol. E3, 1983).

For the use of the N-aminotriazole derivatives Ia and Ib as synergistic agents in accordance with regulations, suitable substituents $R^1$ and $R^2$ are preferably, independently of one another, the following radicals:

alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, alkylthio, preferably substituted in the 1-, 2- or 3-position, in particular 2-ethylthiopropyl; especially straight-chain $C_1$-$C_6$-alkyl;

cycloalkyl, such as cyclopropyl, cyclobutyl, cyclopentyl, cyclohexyl, cycloheptyl and cyclooctyl, in particular cyclopentyl and cyclohexyl;

cycloalkenyl, such as cyclopentenyl, cyclohexenyl, cycloheptenyl and cyclooctenyl, in particular cyclohexenyl; tetrahydropyranyl; norbornyl;

phenyl, biphenyl, naphthyl or pyridyl, where the aromatic radicals may carry from one to five halogen atoms, such as fluorine, chlorine, bromine and iodine, in particular fluorine, chlorine and bromine, and/or from one to three of the following groups:

hydroxyl, phenoxy, nitro, amino, cyano, alkyl of one to four carbon atoms as stated above, in particular methyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl, in particular trifluoromethyl, alkoxy, such as methoxy, ethoxy, propoxy, 1-methylethoxy, butoxy, 1-methylpropoxy, 2-methylpropoxy and 1,1-dimethylethoxy, in particular methoxy, ethoxy, 1-methylethoxy and 1,1-dimethylethoxy, in particular methoxy, haloalkoxy, such as trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy and pentafluoroethoxy, in particular trifluoromethoxy, and/or alkylthio, such as methylthio, ethylthio, propylthio, 1-methylethylthio, butylthio, 1-methylpropylthio, 2-methylpropylthio and 1,1-dimethylethylthio, in particular methylthio,
and their salts which are environmentally compatible and tolerated by crops.

Examples of particularly preferred compounds Ia and Ib are listed in Tables A and B below.

TABLE A

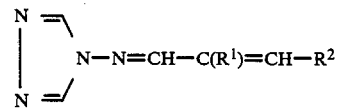
Ia

| $R^1$ | $R^2$ |
|---|---|
| 4-F—$C_6H_4$ | 2-Cl—$C_6H_4$ |
| 4-F—$C_6H_4$ | 3-Cl—$C_6H_4$ |
| 4-F—$C_6H_4$ | 4-Cl—$C_6H_4$ |
| 4-F—$C_6H_4$ | 2,4-Cl,Cl—$C_6H_3$ |
| 4-F—$C_6H_4$ | 2-F—$C_6H_4$ |
| 4-F—$C_6H_4$ | 4-F—$C_6H_4$ |
| 4-F—$C_6H_4$ | 2-Br—$C_6H_4$ |
| 4-F—$C_6H_4$ | 2-OCH$_3$—$C_6H_4$ |
| 4-F—$C_6H_4$ | 2-CH$_3$—$C_6H_4$ |
| 4-F—$C_6H_4$ | 4-NO$_2$—$C_6H_4$ |
| 4-F—$C_6H_4$ | 4-NH$_2$—$C_6H_4$ |
| 4-F—$C_6H_4$ | 2-CF$_3$—$C_6H_4$ |
| 4-F—$C_6H_4$ | 4-CF$_3$—$C_6H_4$ |
| 4-F—$C_6H_4$ | $C_6H_5$—O—$C_6H_4$ |
| 4-F—$C_6H_4$ | 2-naphthyl |
| 4-F—$C_6H_4$ | 3-pyridyl |
| 4-F—$C_6H_4$ | 4-biphenyl |

TABLE A-continued

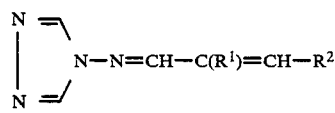
Ia

| $R^1$ | $R^2$ |
|---|---|
| 4-F—$C_6H_4$ | cyclohexyl |
| 4-F—$C_6H_4$ | 3-cyclohexenyl |
| 4-F—$C_6H_4$ | 4-tetrahydropyranyl |
| $C_6H_5$ | $C_6H_5$ |
| $C_6H_5$ | 2-Cl—$C_6H_4$ |
| $C_6H_5$ | 4-Cl—$C_6H_4$ |
| $C_6H_5$ | 2,4-Cl,Cl—$C_6H_3$ |
| $C_6H_5$ | 2-F—$C_6H_4$ |
| $C_6H_5$ | 4-F—$C_6H_5$ |
| $C_6H_5$ | 2-OCH$_3$—$C_6H_4$ |
| $C_6H_5$ | 2-CF$_3$—$C_6H_4$ |
| 2-Cl—$C_6H_4$ | 4-Cl—$C_6H_4$ |
| 2-Cl—$C_6H_4$ | 2,4-Cl,Cl—$C_6H_3$ |
| 2-Cl—$C_6H_4$ | 4-F—$C_6H_4$ |
| 2-Cl—$C_6H_4$ | 2-Br—$C_6H_4$ |
| 2-Cl—$C_6H_4$ | 2-CF$_3$—$C_6H_4$ |
| 4-Cl—$C_6H_4$ | 2-Cl—$C_6H_4$ |
| 4-Cl—$C_6H_4$ | 4-Cl—$C_6H_4$ |
| 4-Cl—$C_6H_4$ | 2-F—$C_6H_4$ |
| 4-Cl—$C_6H_4$ | 4-F—$C_6H_4$ |
| 4-Cl—$C_6H_4$ | 2-Br—$C_6H_4$ |
| 4-Cl—$C_6H_4$ | 2-OCH$_3$—$C_6H_4$ |
| 4-Cl—$C_6H_4$ | 2-CH$_3$—$C_6H_4$ |
| 4-Cl—$C_6H_4$ | 2-CF$_3$—$C_6H_4$ |
| 2,4-Cl,Cl—$C_6H_3$ | 2-Cl—$C_6H_4$ |
| 2,4-Cl,Cl—$C_6H_3$ | 4-Cl—$C_6H_4$ |
| 2,4-Cl,Cl—$C_6H_3$ | 2-F—$C_6H_4$ |
| 2,4-Cl,Cl—$C_6H_3$ | 2-F—$C_6H_4$ |
| 2,4-Cl,Cl—$C_6H_3$ | 4-F—$C_6H_4$ |
| 2,4-Cl,Cl—$C_6H_3$ | 2-CF$_3$—$C_6H_4$ |
| 2,4-Cl,Cl—$C_6H_3$ | 2-OCH$_3$—$C_6H_4$ |
| 2,4-Cl,Cl—$C_6H_3$ | 2-CH$_3$—$C_6H_4$ |
| 4-OCH$_3$—$C_6H_4$ | 2-Cl—$C_6H_4$ |
| 4-OCH$_3$—$C_6H_4$ | 4-Cl—$C_6H_4$ |
| 4-tert.-$C_4H_9$—$C_6H_4$ | 2-Cl—$C_6H_4$ |
| 4-tert.-$C_4H_9$—$C_6H_4$ | 2-F—$C_6H_4$ |
| 4-tert.-$C_4H_9$—$C_6H_4$ | 4-F—$C_6H_4$ |
| 2-naphthyl | 2-Cl—$C_6H_4$ |
| 2-naphthyl | 4-Cl—$C_6H_4$ |
| tert.-$C_4H_9$ | 2-Cl—$C_6H_4$ |
| tert.-$C_4H_9$ | 4-Cl—$C_6H_4$ |
| tert.-$C_4H_9$ | 2-F—$C_6H_4$ |
| tert.-$C_4H_9$ | 4-F—$C_6H_4$ |
| tert.-$C_4H_9$ | 2,4-Cl,Cl—$C_6H_3$ |
| tert.-$C_4H_9$ | 2-CF$_3$—$C_6H_4$ |
| cyclohexyl | 2-Cl—$C_6H_4$ |
| cyclohexyl | 4-Cl—$C_6H_4$ |
| cyclohexyl | 2,4-Cl,Cl—$C_6H_3$ |
| cyclohexyl | 2-F—$C_6H_4$ |
| 4-tetrahydropyranyl | 2-Cl—$C_6H_4$ |
| 4-tetrahydropyranyl | 4-Cl—$C_6H_4$ |
| 4-F—$C_6H_4$ | norbornyl |

TABLE B

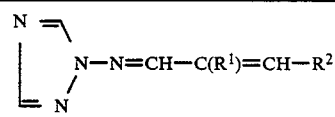
Ib

| $R^1$ | $R^2$ |
|---|---|
| 4-F—$C_6H_4$ | 2-Cl—$C_6H_4$ |
| 4-F—$C_6H_4$ | 4-Cl—$C_6H_4$ |
| 4-F—$C_6H_4$ | 2-Br—$C_6H_4$ |
| 4-F—$C_6H_4$ | 2-CH$_3$—$C_6H_4$ |
| 4-F—$C_6H_4$ | 2-CF$_3$—$C_6H_4$ |
| $C_6H_5$ | 2-Cl—$C_6H_4$ |
| 2-Cl—$C_6H_4$ | 4-F—$C_6H_4$ |
| 4-Cl—$C_6H_4$ | 2-CF$_3$—$C_6H_4$ |
| tert.-$C_4H_9$ | 2-Cl—$C_6H_4$ |
| tert.-$C_4H_9$ | 4-Cl—$C_6H_4$ |
| tert.-$C_4H_9$ | 4-F—$C_6H_4$ |

TABLE B-continued $$\underset{N}{\overset{N}{\underset{\Vert}{\bigvee}}} N-N=CH-C(R^1)=CH-R^2 \qquad Ib$$

| R$^1$ | R$^2$ |
|---|---|
| tert.-C$_4$H$_9$ | 2,4-Cl,Cl—C$_6$H$_3$ |
| cyclohexyl | 4-Cl—C$_6$H$_4$ |
| cyclohexyl | 2,4-Cl,Cl—C$_6$H$_3$ |
| cyclohexyl | 4-F—C$_6$H$_4$ |

The following table contains specific examples of herbicidal benzothiadiazine derivatives of the formula II whose action can be improved by the synergistic N-aminotriazole derivatives Ia and Ib:

TABLE C $$\text{[benzothiadiazinone structure with } N-CH(CH_3)_2, SO_2, R^4, R^5 \text{]} \qquad II$$

| No. | R$^4$ | R$^5$ | Literature |
|---|---|---|---|
| II.001 | H | H | DE-A 1,542,836 |
| II.002 | Cl | H | DE-A 2,444,383 |
| II.003 | F | H | DE-A 2,444,383 |
| II.004 | CH$_3$ | H | DE-A 2,443,901 |
| II.005 | H | Na | DE-A 1,542,836 |
| II.006 | Cl | Na | DE-A 2,444,383 |
| II.007 | F | Na | DE-A 2,444,383 |
| II.008 | CH$_3$ | Na | DE-A 2,443,901 |
| II.009 | Cl | CN | DE-A 2,656,289 |
| II.010 | F | CN | DE-A 2,656,289 |
| II.011 | CH$_3$ | CN | DE-A 2,656,289 |
| II.012 | H | CN | DE-A 2,656,289 |

The amount of synergistically active compound varies, depending on the crop on which the herbicidal benzothiadiazine derivatives of the formula II are used. The ratios are variable over a wide range, and also depend on the structure of the herbicide II and on the crop involved.

Suitable ratios of synergist to herbicidal active ingredient are from 10:1 to 0.01:1, preferably from 6:1 to 0.05:1, and particularly from 4:1 to 0.1:1, parts by weight.

The herbicidal active ingredients and synergistic compounds may be applied separately or together to the leaves and shoots of crop plants and undesired plants. Preferably, the synergistic agent is applied simultaneously with the herbicidal active ingredient. The synergist and herbicidal active ingredient may be applied simultaneously but separately to the field, or one after the other. They may be formulated together or separately as suspensions, emulsions or solutions for use as spray liquors.

The amount of pure active ingredient required, i.e., without formulation auxiliaries, depends on the composition of the stand, the development stage of the plants, on local climatic conditions, and on the application technique employed. Generally, application rates are from 0.25 to 5, and preferably from 0.5 to 2.5, kg/ha.

The crops in which the herbicidal and synergistic agents may be used are essentially those in which the individual active ingredients of the mixture may be employed. In the case of agents containing benzothiadiazinone derivatives of the formula II, examples of such crops are cereals, groundnuts, rice, soybeans, Indian corn, sorghum and peas.

The method of application is also important. If the novel agents are used for combating unwanted plants in crops having insufficient tolerance, special techniques may be employed by means of which the leaves of the crop plants come as little into contact with the agents as possible, whereas the unwanted plants growing between or under the crop plants, or the free area between them, is hit by the agents (post-directed or layby application).

The herbicidal and synergistic agents according to the invention may be mixed and applied with numerous representatives of further herbicidal or growth-regulating active ingredient groups.

In addition to the synergistic action evident when the N-aminotriazole derivatives Ia or Ib are used together with benzolthiadiazines of the formula II, they may also be used as synergists with the following herbicides (trade names in brackets):

5-amino-4-chloro-2-phenylpyridazin-3(2H)-one (Pyrazon)

4-chloro-5-methylamino-2-(trifluoromethylphenyl)-3(2H)-pyridazin-3(2H)-one (Monometfluorazon)

3-(3-chloro-4-methylphenyl)-1,1-dimethylurea (Chlortoluron)

3-(4-bromophenyl)-1-methoxy-1-methylurea (Metobromuron)

3-(4-isopropylphenyl)-1,1-dimethylurea (Isoproturon)

3(3,4-dichlorophenyl)1-methoxy-1-methylurea (Linuron)

3-(3,4-dichlorophenyl)-1,1-dimethylurea (Diuron)

3-(2-benzothiazolyl)1,3-dimethylurea (Methabenzthiazuron)

1,1-dimethyl-3-(3-trifluoromethylphenyl)-urea (Fluometuron)

methyl-2-[3-(4-methoxy-6-methyl-1,3,5-triazin-2-yl)aminocarbonylaminosulfonyl]benzoate) (Metsulfuron-methyl)

methyl-2-[3-(4,6-dimethoxypyrimidin-2-yl)aminocarbonylaminosulfonyl]benzoate (Bensulfuron-methyl)

ethyl-2-[3-(4-chloro-6-methoxypyrimidin-2-yl)aminocarbonylaminosulfonyl]benzoate (Chlorimuron)

methyl-2-[3-(4-methoxy-6-methyl-1,3,5-triazin-2-yl)-3-methylaminocarbonylaminosulfonyl]benzoate 3-(4,6-dimethoxy-1,3,5-triazin-2-yl)-1-[2-(2-methoxyethoxy)phenylsulfonyl]urea (Cinosulfuron)

methyl-2-[3-(4,6-bis(difluoromethoxy)pyrimidin-2-yl)-aminocarbonylaminosulfonyl]benzoate (Primisulfuron)

2-(2-chloroethoxy)N-[[(4-methoxy-6-methyl-1,3,5-triazin-2-yl)aminocarbonyl]benzenesulfonamide (Triasulfuron)

2-[[(4,6-dimethoxypyrimidin-2-yl)aminocarbonyl]aminosulfonyl]-3-pyridinecarboxylic acid-N,N-dimethylamide S-(4-chlorobenzyl)-N,N-diethylthiocarbamate (Benthiocarb)

S-benzyl-N,N-dipropylthiocarbamate (Prosulfocarb)

S-ethyl-N,N,-di-iso-butylthiocarbamate (Butylat)

S-ethyl-N,N-di-n-propylthiocarbamate (EPTC)

3-(methoxycarbonylamino)phenyl-N-(3-methylphenyl)carbamate (Phenmedipham)

3-(ethoxycarbonylamino)phenyl-N-phenylcarbamate (Desmedipham)

isopropyl-N-(3-chlorophenyl)-carbamate (Chloropropham)
2,6-dinitro-N,N-dipropyl-4-trifluoromethylaniline (Trifluralin)
3,4-dimethyl-2,6-dinitro-N-1-ethylpropylanilin (Pendimenthalin)
4-amino-3-methyl-6-phenyl-1,2,4-triazin-5(4H)-one (Metamitron)
4-amino-6-tert.-butyl-3-methylthio-1,2,4-triazin-5(4H)-one (Metribuzin)
2-(2-chloro-4-ethylamino-1,3,5-triazin-yl-amino)-2-methylpropionitrile (Cyanazin)
2-chloro-4-ethylamino-6-iso-propylamino-1,3,5-triazine (Atrazin)
2-chloro-4-ethylamino-6-tert.-butylamino-1,3,5-triazine (Terbutylazin)
3-chloro-4-chromethyl-1-(3-trifluoromethylphenyl)pyrrolidin-2-one (Fluorochloridin)
2-chlor-6-nitro-3-phenoxyaniline (Aclonifen)
3,6-dichlor-2-methoxybenzoic acid (Dicamba)
2,5-dichloro-3-aminobenzoic acid (Amiben)
2,4-dichlorophenoxyacetic acid (2,4-D)
2-(2,4-dichlorophenoxy)propionic acid (Dichloprop)
2-(4-chloro-2-methylphenoxy)propionic acid (Mecoprop)
methyl-[4-(2,4-dichlorophenoxy)-phenoxy]propionate (Diclofop-methyl)
ethyl-2-[4-(6-chloro-2-benzoxazolyloxy)phenoxy]propionate (Fenoxaprop-ethyl)
ethyl-2-[4-(6-chloro-2-quinoxanyloxy)phenoxy]propionate (Quizalafop-ethyl)
methyl-2-[4-(3-chloro-5-trifluoromethyl-2-pyridyloxy)-phenoxy]propionate (Haloxyfop-methyl)
butyl-2-[4-(5-trifluoromethyl-2-pyridyloxy)phenoxy]-propionate (Fluazifop-bentyl)
4-amino-3,5-dichloro-6-fluoro-2-pyridinyloxyacetic acid-1-methylheptyl ester (Fluroxypyr)
7-chlor-3-methylquinoline-8-carboxylic acid (Quinmerac)
3,7-dichloroquinoline-8-carboxylic acid (Quinchlorac)
N-(2,4-difluorophenyl)-2-(3-trifluoromethylphenoxy)-3-pyridincarboxamide (Diflufanican)
exo-1-methyl-4-(1-methylethyl)-2(2-methylphenylmethoxy)-7-oxabicyclo(2.2.1)heptane (Cinmethlin)
2-(2-chlorophenyl)methyl-4,4-dimethyl-3-is-oxazolidinon (Clomazon)
5-methylamino-2-phenyl-4-(3-trifluoromethylphenyl)-furan-3(2H)-one (Flurtamon)
2-[4,5-dihydro-4-methyl-4-(1-methylethyl)-5-oxo-1H-imidazol-2-yl]-5-ethyl-3-pyridine carboxylic acid (Imazethapyr)
2-[4,5-dihydro-4-methyl-4-(1-methylethyl)-5-oxo-1H-imidazol-2-yl)-3-quinolinecarboxylic acid (Imazaquin)
4-chloro-2-oxobenzothiazolin-3-ylacetic acid (Benazolin)
2-phenyl-3,1-benzoxazin-4-one
5-fluoro-2-phenyl-4H-3,1-benzoxazin-4-one (Fluorobentranie)
3',4'-dichloropropionanilide (Propanil)
5-[2-chloro-4-(trifluoromethyl)phenoxy]-2-nitrobenzoic acid, sodium salt (Acifluorfen)
methyl-5-(2,4-dichlorophenoxy)-2-nitrobenzoate (Bifenox)
5-(2-chloro-4-trifluoromethylphenoxy)-2-nitro-N-methansulfonylbenzamide (Fomesafen)
3,5-dibromo-4-hydroxybenzonitrile (Bromoxynil)
3,5-diiodo-4-hydroxybenzonitrile (Ioxynil).

It may also be useful to apply the mixtures according to the invention in admixture with other crop protection agents, e.g., agents for combating pests or phytopathogenic fungi or bacteria. The mixtures may also be mixed with solutions of minerals used to remedy nutritional or trace element deficiencies.

The agents according to the invention, or the herbicidal active ingredient and the synergist when applied separately, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

The formulations contain from 0.1 to 95, and preferably from 0.5 to 90, wt % of active ingredient mixture, and may be produced by conventional methods.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the herbicidal active ingredient and/or antidote as such or dissolved in an oil or solvent may be homogenized in water by means of wetting or dispersing agents, adherents or emulsifiers. Concentrates which are suitable for dilution with water may be prepared from herbicidal active ingredient and/or antidote, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the herbicidal active ingredient and/or antidote with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

MANUFACTURING EXAMPLES

The directions given in the examples below were employed, after appropriate modification of the starting materials, for obtaining further compounds of the formulae Ia and Ib; the compounds obtained are listed with their physical data in Tables 1 and 2 below.

EXAMPLE 1

1-(2-Chlorophenyl)-2-(4-fluorophenyl)-3-(1,3,4-triazol-1-yl)-aminopropane

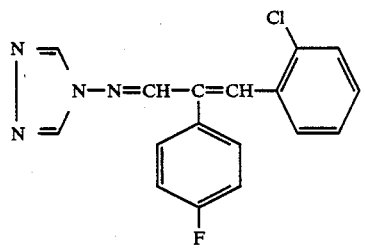

at 25° C., 168 g of N-amino-1,3,4-triazole was added to a solution of 260.5 g of 3-(2-chlorophenyl)-2-(4-fluorophenyl)-propenal in 1,500 ml of toluene, and the reaction mixture was refluxed for 48 hours. Water was then added to the mixture, the product being obtained as a solid.

Yield: 179 g (55%); m.p.: 198°–200° C.; active ingredient no. 1.001

TABLE 1

$$\begin{array}{c} N = \\ | \quad N-N=CH-C(R^1)=CH-R^2 \\ N = \end{array} \quad \text{Ia}$$

| Active ingredient no. | R¹ | R² | Phys. data mp. (°C.); ¹H—NMR (δ in ppm) |
|---|---|---|---|
| 1.001 | 4-F—C₆H₄ | 2-Cl—C₆H₄ | 198–200 |
| 1.002 | C₆H₅ | 2-Cl—C₆H₄ | 180–182 |

TABLE 2

$$\begin{array}{c} N = \\ | \quad N-N=CH-C(R^1)=CH-R^2 \\ N \end{array} \quad \text{Ib}$$

| Active ingredient no. | R¹ | R² | Phys. data mp. (°C.); ¹H—NMR (δ in ppm) |
|---|---|---|---|
| 2.001 | 4-F—C₆H₄ | 2-Cl—C₆H₄ | 153–155 |
| 2.002 | C₆H₅ | 2-Cl—C₆H₄ | 96–101 |

USE EXAMPLES

The influence of various representatives of the herbicidal agents according to the invention, or combinations consisting of herbicide and synergist, on the growth of unwanted and crop plants compared with the influence of the herbicidal active ingredient alone is demonstrated by the following biological examples from greenhouse experiments:

Plastic flowerpots having a volume of approx. 300 cm³ and filled with a sandy loam containing about 3% humus were used for growing the test plants. The seeds of the test plants were sown shallow, and separately according to species, and were then watered. The vessels were then covered with transparent plastic hoods until the seeds had germinated uniformly and the plants had taken root.

For the postemergence treatment, the test plants were grown to a height of from 3 to 20 cm, depending on growth form, before being treated. The herbicidal agents were suspended or emulsified in water as vehicle and sprayed through finely distributing nozzles.

The benzothiadiazine derivative II used in the biological examples was II.005

The herbicidal active ingredient II.005 was applied as a commercially formulated product (480 g/l of emulsion concentrate).

All the synergistically active compounds were formulated with 10 wt % of active ingredient in a mixture consisting of 70% of active ingredient, 20% of emulsifier and 10% of surfactant.

Where the herbicide and synergist were applied together, the individual formulations described above were mixed beforehand.

The vessels were set up in the greenhouse - heat-loving species at 18° to 35° C. and species from more moderate climates at 10° to 25° C.

The experimental period was 3 to 5 weeks. During this period the plants were tended and their reactions to the various treatments assessed. Damage caused by the chemical agents was evaluated on a 0% to 100% scale, compared with the untreated control plants, 0 denoting no damage and 100 complete destruction of the plants.

In the following examples, the action of the agents to be used in accordance with the invention is illustrated without excluding the possibility of further applications.

In these examples, the method of S. R. Colby (Weeds 15, 20) was used to calculate the value E which is to be expected if the combined action of the individual components of the mixture is merely additive.

The formula employed is $$E = X + Y - \frac{XY}{100}$$

where X is the percentage action with preparation a at application rate a; Y is the percentage action with preparation B at application rate b; and E is the expected action (in %) of a+B at application rates a+b.

If the figure observed is higher than the value E calculated according to Colby, the action is synergistic.

The tables below document the synergistic action of compound 1.001, as a result of which the herbicidal action of active ingredient II.005 on an unwanted plant is considerably improved without the crop plant being damaged.

TABLE 3

Synergistic action of compound 1.001 according to the invention on joint application with herbicidal active ingredient II.005

| Appl. rate [kg/ha] | | Amaranthus retroflexus | |
|---|---|---|---|
| Example No. 1.001 | Herbicide II.005 | Damage [in %] | E [after Colby] |
| — | 1.25 | 55 | — |
| — | 0.625 | 45 | — |
| — | 0.313 | 35 | — |
| 0.25 | — | 0 | — |
| 0.25 | 1.25 | 100 | 55 |
| 0.25 | 0.625 | 90 | 45 |
| 0.25 | 0.313 | 88 | 35 |

TABLE 4

Synergistic action of compound 1.001 according to the invention on joint application with herbicidal active ingredient II.005

| Appl. rate [kg/ha] | | Test plants [Damage in %; E after Colby] | | | |
|---|---|---|---|---|---|
| Example No. 1.001 | Herbicide II.005 | Glycine max. | E | amaranthus retroflexus | E |
| — | 1.25 | 0 | — | 95 | — |
| — | 0.625 | 0 | — | 58 | — |
| — | 0.313 | 0 | — | 35 | — |
| — | 0.156 | 0 | — | 20 | — |
| 0.125 | — | 0 | — | 0 | — |
| 0.125 | 1.25 | 0 | 0 | 100 | 95 |
| 0.125 | 0.625 | 0 | 0 | 100 | 58 |
| 0.125 | 0.313 | 0 | 0 | 98 | 35 |
| 0.125 | 0.156 | 0 | 0 | 85 | 20 |

*all sprays additionally contained 2.8 l/ha of spray oil concentrate as surfactant additive.

We claim:

1. An N-aminotriazole derivative of the formulae Ia or Ib

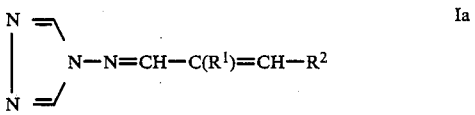

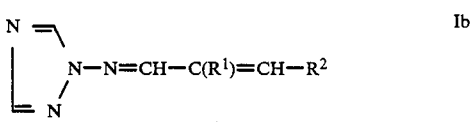

where $R^1$ and $R^2$ are each selected from the group consisting of $C_1$-$C_8$-alkyl, $C_3$-$C_8$-cycloalkyl, $C_5$-$C_8$-cycloalkenyl, tetrahydropyranyl, norbornyl, phenyl, biphenyl, naphthyl and pyridyl, and the aromatic radicals may be substituted with one to five halogen atoms or one to three hydroxy, phenoxy, nitro, amino, cyano, $C_1$-$C_4$-alkyl, $C_1$-$C_4$-haloalkyl, $C_1$-$C_4$-alkoxy, $C_1$-$C_4$-haloalkoxy or $C_1$-$C_4$-alkylthio radicals, and their salts which are environmentally compatible and tolerated by crops.

2. An N-aminotriazole derivative of the formulae Ia or Ib according to claim 1, where $R^1$ and $R^2$ are each phenyl which may be substituted with one to three halogen atoms or one to two methyl, difluoromethyl, trifluoromethyl, methoxy, difluoromethoxy, trifluoromethoxy or methylthio radicals.

3. A compound of the formula Ia as defined in claim 1, wherein $R^1$ is 4-F-$C_6H_4$ and $R^2$ is 2-Cl-$C_6H_4$.

* * * * *